United States Patent
Devlin et al.

(10) Patent No.: US 6,187,026 B1
(45) Date of Patent: *Feb. 13, 2001

(54) SURGICAL INSTRUMENTS (75) Inventors: Stuart Leslie Devlin, Angmering-on-Sea; Ian Trevor Dampney, London, both of (GB)

(73) Assignee: Atraumatic Limited, West Sussex (GB)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/875,934
(22) PCT Filed: Jan. 25, 1996
(86) PCT No.: PCT/GB96/00161
  § 371 Date: Mar. 17, 1998
  § 102(e) Date: Mar. 17, 1998
(87) PCT Pub. No.: WO96/24298
  PCT Pub. Date: Aug. 15, 1996

(30) Foreign Application Priority Data

Feb. 9, 1995 (GB) ................................. 9502498.0

(51) Int. Cl.[7] ................................................ A61B 17/28
(52) U.S. Cl. .......................................................... 606/205
(58) Field of Search .................... 606/205, 206, 606/207, 208, 209, 210

(56) References Cited

U.S. PATENT DOCUMENTS

| | | |
|---|---|---|
| 3,746,814 | 7/1973 | Lackey . |
| 4,258,716 | 3/1981 | Sutherland . |
| 4,433,687 | 2/1984 | Burke . |
| 4,760,848 | 8/1988 | Hasson . |
| 5,176,700 | 1/1993 | Brown . |
| 5,195,507 | 3/1993 | Bilweis . |
| 5,290,302 | 3/1994 | Pericie . |
| 5,338,317 | 8/1994 | Hasson . |
| 5,355,871 | * 10/1994 | Hurley et al. ................ 606/205 |
| 5,370,658 | 12/1994 | Scheller . |
| 5,549,627 | * 8/1996 | Kieturakis ................ 606/205 |
| 5,792,165 | * 8/1998 | Klieman et al. ................ 606/206 |

FOREIGN PATENT DOCUMENTS

| | | |
|---|---|---|
| 2460481 | 6/1976 | (DE) . |
| 3526821 | 2/1987 | (DE) . |
| 4211417 | 1/1993 | (DE) . |
| 4131494 | 4/1993 | (DE) . |
| 0217559 | 4/1987 | (EP) . |
| 2701832 | 9/1994 | (FR) . |

* cited by examiner

Primary Examiner—Michael Buiz
Assistant Examiner—Tan-Uyen T. Ho
(74) Attorney, Agent, or Firm—Wolf, Greenfield & Sacks, P.C.

(57) ABSTRACT

The invention provides a surgical instrument comprising a handle (1) shaped to enable it to be freely rotated by the user's fingers about its longitudinally axis in the hand of the user, and held by the user at any angle of rotation about its longitudinal axis; the handle (1) having an elongate shaft (2) extending therefrom and a surgical tool (3) mounted on the shaft (2) at a location remote from the handle (1); the handle (1) being provided with actuato means (20, 15, 29) operatively linked through the shaft (2) to the surgical tool (3); the actuator means having an actuator surface (17, 31) or surfaces extending around substantially the entire circumference of the handle (1), whereby the actuator means is operable by applying pressure at substantially any circumferential location on the actuator surface (17, 31) or surfaces, to actuate the surgical tool (3). The surgical instrument is designed particularly to be held in a pen-like grip, rather than in the palm of the hand or in a scissors grip as is conventional, and is desined to be actuated from any rotated position.

28 Claims, 7 Drawing Sheets

SURGICAL INSTRUMENTS

FIELD OF THE INVENTION

This invention relates to surgical instruments, for use in laparoscopic or endoscopic surgery and/or open surgery.

BACKGROUND OF THE INVENTION

Laparoscopic and endoscopic surgical methods have become increasingly popular in recent years. Such methods typically involve making small incisions in the abdominal wall of a patient through which specially designed laparoscopic or endoscopic tools are inserted for carrying out the surgical procedure. Such tools typically have a miniaturised surgical implement such as forceps or scissors at the end of a long shaft to the other end of which is attached a handle and actuating mechanism. By the use of such tools, the surgeon can operate the instrument from outside the patient's body whilst monitoring the movement of the surgical tool within the body by means of an endoscope.

Such techniques of minimally invasive therapy (MIT), which have been commonly referred to as keyhole surgery, offer very substantial advantages over conventional open surgery in that only very small incisions in the patient's body wall are required thus substantially minimising patient trauma, dramatically reducing post-operative complications, and greatly reducing the opatient's recovery time.

As laparoscopic or endoscopic surgical techniques are generally more delicate than those of open surgery, the surgical instruments need to be particularly easy in manipulate and use. Hitherto, the surgical instruments used in MIT have been cumbersome to use. For example, many conventional laparoscopic instruments have off-centre scissor handles for actuating the surgical tool. The presence of such scissor-handle actuated mechanisms makes steady control and rotation of the instrument difficult. To overcome this problem, some tools are provided with a thumb wheel by which the actuator shaft is rotated independently from the scissor handles. However, such an arrangement is clumsy to use and often requires two hands to operate effectively. Thus, there remains a need for surgical instruments for use in surgery which are more easily manipulated, can be operated entirely by one hand, can be rotated freely, and operated just as effectively in any rotated position to enable the orientation of the surgical tool to be varied as required. It is an object of the present invention to provide such an instrument.

SUMMARY OF THE INVENTION

The present invention is based in part on the recognition that a surgical instrument can be manipulated with greater control and sensitivity when the instrument is held in a pen-like grip, i.e. with the non-functioning end of the instrument extending rearwardly from between the thumb and forefinger. Furthermore, the invention is based on the recognition that a surgical instrument can be made more responsive and easier to use if it can be rotated by the fingers to any position and can be actuated from a position anywhere around the circumference of the handle of the instrument. This is in contrast to existing surgical tools such as those disclosed in, for example EP-A-0535370 and EP-A-0598202, in which either a squeeze grip type actuation mechanism is provided, or an actuator lever is provided at a single location on the circumference of the instrument handle.

Accordingly, in a first aspect the invention provides a surgical instrument comprising a handle shaped to enable it to be freely rotated by the user's fingers a-cut its longitudinal axis in the hand of the user, and held by the user at any angle of rotation about its longitudinal axis; the handle having an elongate shaft extending therefrom and a surgical tool mounted on the shaft at a location remote from the handle; the handle being provided with actuator means operatively linked through the shaft to the surgical tool; the actuator means having an actuator surface or surfaces extending around substantially the entire circumference of the handle, whereby the actuator means is operable by applying pressure at substantially any circumferential location on the actuator surface or surfaces, to actuate the surgical tool.

The handle may be of generally circular cross-section, or it may be of a non-circular cross-section. For example it may be of polygonal cross-section, eg hexagonal or octagonal, but most preferably it is circular in cross-section. The term circumference as used herein is intended to refer to the perimeters of both circular and non-circular handles.

The actuator surface may be a continuous surface extending around the circumference of the handle or it may, alternatively, comprise an array of closely spaced discrete actuator elements.

The actuator means may be mechanical, electrical, pneumatic or hydraulic or any combination of these.

In one particular example of a mechanical arrangement, the actuator means is mechanically linked to an actuating rod disposed slidably within the elongate shaft, which rod is in turn linked to the surgical tool on the end of the shaft.

In one particular example of an electrical arrangement, the actuator means may comprise a switch or array of switches for controlling the flow of electrical current along the shaft to a diathermy tool (e.g. a diathermy hook) at the end thereof.

The surgical tool mounted at the end of the elongate shaft may be any one of the types of surgical tools conventionally used in laparoscopic or endoscopic surgery. Thus, for example, the surgical tool may be a miniaturised surgical instrument such as a pair of forceps, a clamp, a pair of scissors or a diathermy hook. Any of the aforesaid tools may optionally have a monopolar or bipolar diathermy capability.

The actuator means in one embodiment can be an array of radially displaceable actuator elements disposed around the circumference of the handle, means being provided for converting radial inward movement of an actuator element into longitudinal movement of the actuating roc within the elongate shaft.

For example, the actuator element may be provided with an edge or surface which functions as a cam follower or camming surface, for engaging and camming against a complimentary camming surface or cam follower associated with the actuating rod.

In one embodiment, each actuator element is provided with a wedging member having an inclined surface whereby radially inward movement of the actuator element urges the inclined surface of the wedging member into contact with a camming edge or surface associated with the actuator shaft, thereby to displace the camming edge or surface in a longitudinal direction.

A sufficiently large number of actuator elements are disposed around the circumference of the handle to ensure that the instrument can be actuated from substantially any location around its circumference. For this purpose, a minimum of three actuator elements is generally required, but preferably there are more than three actuator elements disposed around the circumference, more preferably there are at least six actuator elements, and in one particularly preferred embodiment there are eight actuator elements. In another particularly preferred embodiment, there are twelve actuator elements.

The handle is preferably of elongate form and is sufficiently small in cross section to enable it to be held in a pen-like grip, i.e. wherein the end of the handle remote from the actuator shaft extends away from the hand between the thumb and adjacent finger.

The handle may typically have a bulbous shape, being tapered towards the end remote from the surgical tool, increasing in diameter towards the central portion thereof and tapering again towards the actuator shaft. The actuator means typically is located within the bulbous or enlarged diameter central region of the handle.

The handle may be provided with means for effecting locking of the surgical tool in a given configuration. For example, where the surgical tool is in the form of a miniature pair of grasping forceps or a clamping tool, the locking means may be effective to lock the forceps or clamping tool in a clamping or gripping configuration.

In one embodiment, the handle is provided with first actuator means for effecting movement of a surgical tool at the end of the actuator shaft from a rest position to an actuated position; locking means for locking the surgical tool in the actuated position; and second actuator means operable to release the locking means to enable the surgical tool to return to the rest position.

Where the actuator means is mechanically linked to an actuating rod disposed slidably within the elongate shaft, which rod is in turn linked to the surgical tool on the end of the shaft, the locking means can take the form of a grasping member having a plurality of grasping portions which grasp the actuating rod to lock it in an actuated position, the second actuator means being operable to force the said grasping portions apart to release the grip on the actuating rod.

The actuating rod may be provided with a spiral track (e.g. a thread) or an array of annular ridges, which cooperate with the grasping portions to form a ratchet mechanism, the spiral track (e.g. thread) being preferred because many more grasping positions are possible within the same linear movement of the actuating rod.

The second actuator means is preferably arranged to be actuable from substantially any position around the circumference of the handle.

The advantages of the surgical instruments of the present invention reside in their ease of manipulation and lightness, and in particular in the ease with which the surgical tool can be rotated and actuated at any rotated position. The ability of the surgical instruments of the invention to be held in a pen-like grip, rather than in the palm of the hand, or in a scissors grip as is conventionally the case, and to be actuated from any rotated position, means that the tool can be operated with much greater sensitivity thereby enabling surgical procedures to be carried out more accurately, safely, efficiently and with reduced surgeon fatigue.

In another aspect, the invention provides an actuator device comprising an actuating rod movable in a reciprocating manner along an axis, the actuating rod having a grasping region defined by a length of the rod having a spiral track (eg a thread) at the surface thereof; biasing means for resiliently biasing the actuating rod in a first direction; actuator means for moving the actuating rod in a second direction opposite to the first direction against a restoring force of the biasing means; grasping means comprising a plurality of grasping portions for grasping the actuating rod at the grasping region to hold the rod in an actuated position against the said restoring force; and grasp releasing means for releasing the actuating rod from the grassing means, The plurality of grasping portions typically takes the form of an annular array of radially inwardly directed grasping fingers formed from a resilient material (e.g. a metal disc spring); the clearance between the radially innermost edges of opposing grasping fingers being less than the diameter of the actuating rod; such that as the actuating rod is urged through the grasping means in one direction, the grasping fingers engage the spiral track at the surface of the actuating rod to prevent movement of the actuating rod in the reverse direction.

The grasp releasing means can take the form of a grasp releasing member having a conical or frustoconical surface which can be urged in an axial direction against the grasping fingers to lift them away from the spiral track to release the actuating rod.

The actuator device is particularly useful in the context of the surgical instruments of the present invention, but may well find uses in other technical fields.

BRIEF DESCRIPTION OF THE DRAWINGS

The invention will now be illustrated but not limited, any reference to the specific embodiments shown in the accompanying drawings, of which.

DESCRIPTION OF THE PREFERRED EMBODIMENT

Figure 1:
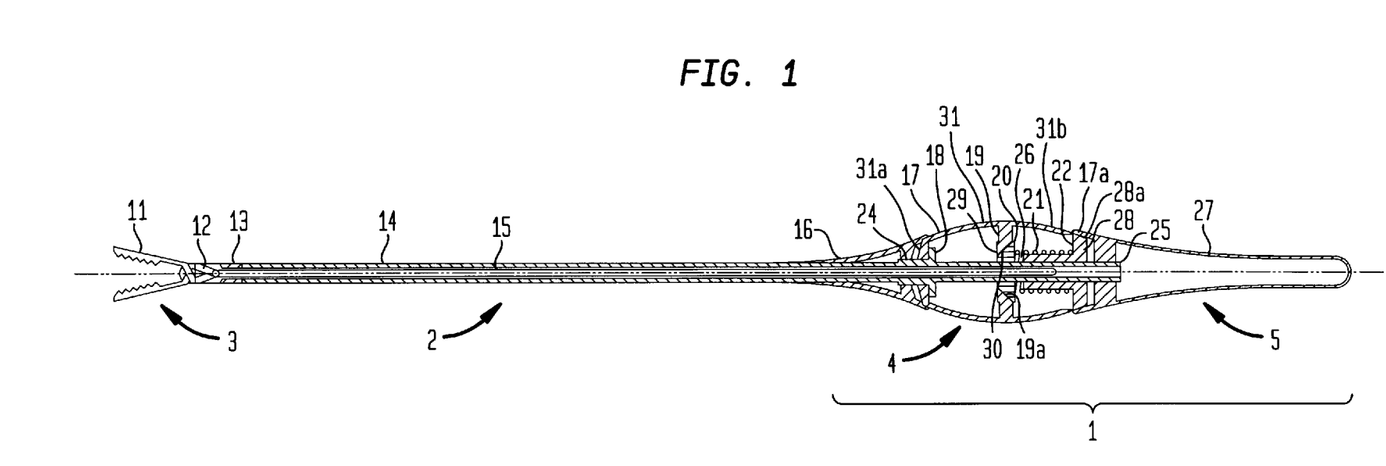
FIG. 1 is a side sectional elevation of a surgical instrument according to one embodiment of the invention.
Figure 2:
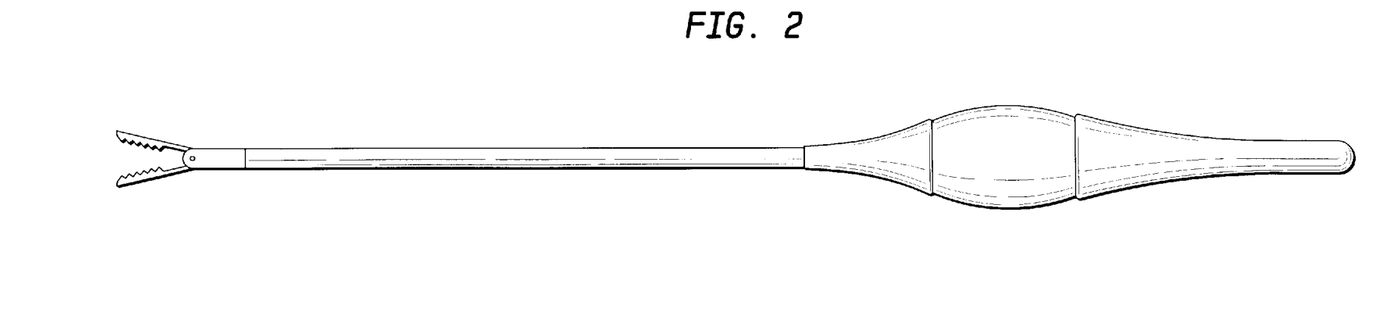
FIG. 2 is a side elevation of the embodiment shown in FIG. 1.

Referring now to FIGS. 1 and 2 it can be seen that the surgical instrument according to one embodiment of the invention comprises an elongate handle 1 having a shaft 2 extending from one end thereof, and a surgical tool 3 mounted at the distal end of the shaft 2. The handle 1 in this embodiment is of elongate form and has a bulbous region 4 from which extends the shaft 2, and a tapering handle extension 5. In use, the tool is grasped between thumb, forefinger and the middle finger, as one would grip a pen, with the end 5 of the instrument extending rearwardly between the thumb and forefinger. The bulbous region 4 conceals an actuator assembly, the details of which can be seen in FIG. 1.

Referring now to FIG. 1, it can be seen that the elongate shaft 2 comprises an outer effector tube 14 having slidably disposed within the hollow interior thereof an actuating rod 15. A surgical tool housing 13 is mounted in the end of effector tube 14, e.g. by silver soldering, a pair of forceps jaws 11 being pivotably mounted on the tool housing 13. The forceps jaws 11 are linked via forceps linkage 12 to the distal end of the actuating rod 15.

The other end of the effector tube 14 extends into and through the bulbous region 4 of the handle 1. The effector tube 14 is provided with a radial flange 18 with an external thread 24 which mates with the internal thread of the generally conical junction member 16. The proximal end 25 of the effector tube is also provided with an external thread upon which is mounted the pen-handle tail-piece 27. The portion of the effector tube 14 passing through the bulbous region 4 of the handle 1 is provided with a slot 26 which allows a cam wheel actuator 20 to be fixedly mounted on the actuating rod 15, the slot 26 having a sufficiently large axial dimension to enable the cam wheel actuator 20 to slide forward and backwards in a reciprocal manner in the slot. Attached to the outer surface of the effector tube 14, to the rear of the slot 26, is an annular collar 22 which has a radial flange 28 extending from the rear part thereof. A return spring 21 is mounted on the annular collar 22 and abuts against the flange 28 and the cam wheel actuator 20 so as to bias the cam wheel actuator 20 towards the front of the slot 26.

Cam wheel actuator 20 has a plurality of inclined surfaces 29 around its outer circumference, each inclined surface 29 being separated from an adjacent inclined surface by means of a pair of axially aligned dividing walls 30.

Disposed radially outwardly of the cam wheel actuator 20 is an array of actuating fingers 19 each of which has an inclined camming surface 19a complementary to the inclined surfaces 29 of the cam wheel actuator. The actuating fingers 19 are mounted on generally flexible actuating arms 31 which have a generally arcuate profile in cross-section and which are joined together at the distal end of the bulbous region 4 and secured to the effector tube 14 by cramping between the conical junction member 16 and the flange 18. Thus, each actuating arm 31 is radially connected to a common hub 31a which is of thicker cross-section than the arcuate portion, the thicker hub 31a resting in front of flange 18. Disposed around the outside of the array of actuator arms 31 is a flexible skin or boot 17 which encases the inner workings of the actuation mechanism. The boot 17, which may be formed from an appropriately flexible plastics material, has an in-turned end portion which, together with hub 31a, is clamped against flange 18 by screwing the threaded junction member 16 tightly onto the external thread 24 of the radial flange 18.

The other end 31b of each actuator arm 31 is unsecured, but the end 17a of the boot 17 is clamped between the outer inclined surface 28a of flange 28 and the inner surface of the handle extension piece 5 as the handle extension piece 5 is screwed onto the threaded end 25 of the effector tube 14.

In use, in order to cause the jaws of the forceps to close, the user of the instrument depresses any one or more of the actuator arms 31 thereby to urge the actuating finger 19 towards the cam wheel actuator. As the actuating finger 19 comes into contact with the cam wheel actuator, the inclined camming surface 19a of the actuating finger cams along the inclined surface 29 of the cam wheel actuator thereby forcing the actuator wheel to move rearwardly along the slot 26. Since the cam wheel actuator is fixed to the actuating rod 15, this has the effect of moving the rod 15 in a rearwards direction thereby causing the jaws of the forceps to close.

Once the pressure is released on the actuating arms 31, the force of the return spring 21 urges the cam wheel actuator forwardly back along the slot to its rest position, thereby causing the actuating rod 15 to move forwardly with it, and thus opening the jaws of the forceps.

The embodiment of the invention illustrated in FIGS. 1 and 2 can be formed from a combination of materials. Thus, normally the forceps jaws 11, forceps linkage 12, linkage housing 13, effector tube 14 and actuating rod 15 would be formed of surgical quality stainless steel but they need not be; instead other metals or an appropriately tough form of sterilisable plastics material may be used. The remaining components can be made either from a suitable metal or from a suitable sterilisable plastics material.

By making the instrument or parts thereof from a plastics material, the tool may be made lighter in weight and possibly cheaper to produce. Thus, a surgical instrument may be made fully disposable thereby avoiding the problems of the build up of contaminants within the instrument that can occur with tools intended for long term reuse.

Whether the instruments of the invention may be designed to be disposable or reusable, they should be formed from materials which are capable of withstanding the autoclaving or other sterilisation procedures typically used for surgical instruments. For autoclaving, such materials should preferably have the ability to withstand temperatures in excess of 134° without deforming or otherwise losing their integrity during the sterilising process.

One potential problem with surgical instruments used in laparoscopic techniques, and employing a coaxial actuator shaft arrangement, is that contaminants such as blood and other bodily fluids can migrate along the space between the inner and outer shafts and removal of such contaminants can be very difficult without dismantling the equipment after each use. In order to avoid this potential problem, in the instruments of the present invention, a sealing means may be provided between the actuator rod and effector tube to prevent or reduce substantially the likelihood of contaminants finding their way into the very small annular gap between the two. The sealing means could, for example, take the form of an O-ring or other seal formed from a low friction material which does not hinder movement of the actuator rod along the bore of the effector tube.

In order to eliminate completely the possibility of contaminants moving along the gap between the inner and outer coaxial shafts, the actuating rod may be provided with a flexible skirt which in turn is connected to the inner wall of the effector tube. The skirt acts as a barrier to contaminants.

Alternatively, the instrument may be constructed so as to be dismantled for cleaning and sterilising purposes.

The actuator mechanism illustrated in FIGS. 1 and 2 is a simple "open and close" mechanism. However, in many instances, it may be desirable that the actuator mechanism should provide some form of locking means for locking the jaws of the tool in the gripping or closed position.

Figure 3:
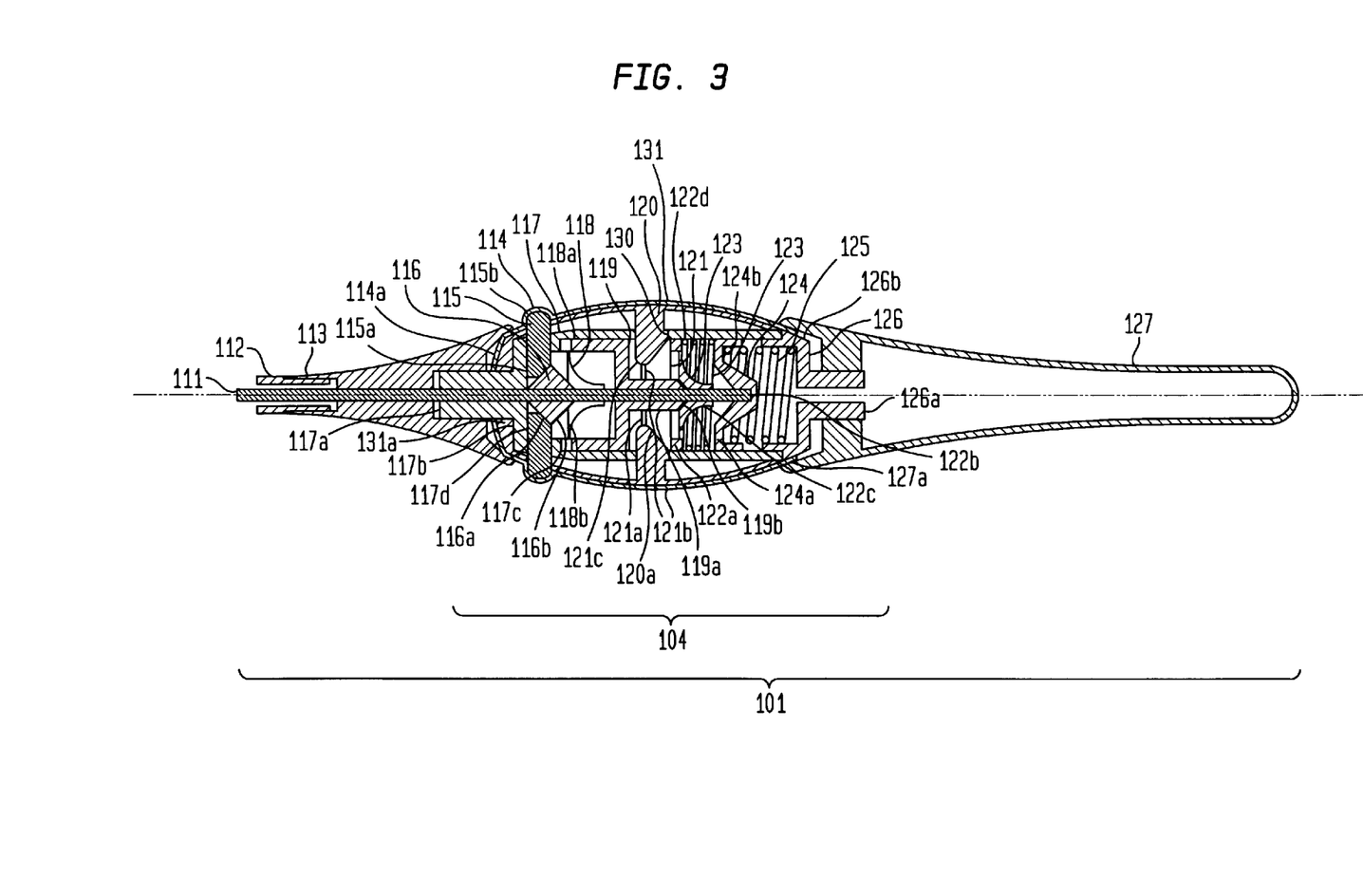
FIG. 3 is a side sectional elevation of the handle portion of a surgical instrument according to a second embodiment of the invention.

A second embodiment of the invention, which has such a lacking facility, is shown in FIG. 3.

The instrument, of which the handle is shown in FIG. 3, is similar in external appearance but has a modified actuator arrangement within the handle. Thus, as with the instrument shown in FIGS. 1 and 2, the instrument has an elongate handle 101, and an actuator shaft with a surgical tool (not shown) mounted at its end. The handle 101 is shaped to enable it to be held in a pen-like grip between thumb, forefinger and index finger and has a bulbous region 104 at approximately its mid-point, and a pen handle tail piece 127. The bulbous portion conceals the actuator mechanism.

As with the embodiment of FIGS. 1 and 2, the shaft comprises an outer effector tube 112 and an actuating rod 111 slidably disposed within the effector tube 112. The effector tube 112 has a threaded end which screws into a threaded socket at the distal end of junction member 113. The actuating rod 111 on the other hand extends through a central bore in the junction member 113 and into the interior of the bulbous portion 104 where the actuating mechanism is located.

The actuation mechanism comprises a generally cylindrical housing 117, hereinafter referred to as the actuator retaining capsule. The actuator retaining capsule 117 has a threaded boss or spigot 117a extending axially from one end thereof, onto which is screwed the junction member 113. At the other end, i.e. the end furthest from the shaft 12, the actuator retaining capsule 117 is provided with an end piece 126 which fits tightly within the rearwardly facing open end of the capsule 117 and is secured therein by means of three small radially positioned screws (not shown). Alternatively, end piece 126 and capsule 117 can be secured together by means of a threaded union, adhesive, welding or by any other common fixing method.

End piece 126 has extending axially rearwardly therefrom a threaded spigot or boss portion 126a onto which is screwed the internally threaded pen handle tail piece 127 which is of elongate tapering form and, in this embodiment, is hollow for lightness.

Fixedly mounted (in this case by means of three small screws) within the actuator retaining capsule 117 is actuator cam release member 119. Actuator cam release member 119 has a rearwardly oriented spigot portion 119a which has a radially inwardly inclined end surface 119b, the purpose of the inclined end surface 119b being to assist in the dismantling of the instrument as will be described below. Spigot portion 119a serves as a support upon which is slidably mounted cam wheel actuator 121. Cam wheel actuator 121 has a plurality of inclined surfaces 121a separated by means of axially aligned dividing walls 121b. Each pair of adjacent dividing walls 121b and the inclined surface 121a therebetween define a camming slot 121c on the cam wheel. To the rear (i.e. furthest from the shaft) of the cam wheel actuator 121 is a grasping element or actuating cam wheel 122. The grasping element or actuating cam wheel 122 has a radially outer annular portion 122a which abuts against the inner surface of the actuator retaining capsule 117. Extending radially inwardly from the annular portion 122a are a plurality of grasping cams, each of which has a grasping portion 122c. The radially inner surfaces of each grasping portion 122c are provided with grooves 122b of a radius smaller than the radius of actuating rod 111 so as to enable the grasping cams to more positively grasp the actuating rod 111. In order to further enhance the grip of the grasping portions on the actuating rod 111. the surface of the actuating rod 111 may be roughened.

Disposed rearwardly of the actuating cam wheel 122 is an annular member 124 which is arranged for sliding movement within the actuator retaining capsule 1,7. Annular member 124 has a central recess for accommodating the end of actuating rod 111. A first return spring 123 is arranged between a front face 124a of the annular member and a rear face 122d of the annular portion 122a of the actuating cam wheel 122 so as to bias the actuating cam wheel against the cam wheel actuator 121.

Extending between the rear surface 124b of the annular member 124 and an end wall of the end piece 126 is a second return spring 125 which is of greater stiffness than the first return spring 123.

The actuator retaining capsule 117 is provided with an array of slots 130 around its circumference at approximately its mid-point. Located outside the actuator retaining capsule 117 are a plurality of axially aligned actuating arms 131 arranged in an array around the circumference of the handle. In this embodiment, eight actuating arms 131 are provided although a smaller or greater number may be provided as desired. Each actuating arm is radially joined to a common hub 131a of wedge-shaped cross-section (e.g. by virtue of being integrally formed with the hub), the hub 131a being clamped between the junction member 113 and the end wall 117b of the capsule 117. The rearward end of each actuating arm 131 is not clamped but is held in place by means of the outer skin or boot 114 which is formed of a flexible material and encloses and seals the entire bulbous portion. The boot is held in place by virtue of its in-turned end 114a being clamped between junction member 113 and the end wall 117b of the capsule 117, and its rearward end being clamped between the inclined surface 126b of the capsule end portion 126 and the inner surface 127a of the tail piece.

Extending radially inwardly from about the mid-point of each actuating arm 131 is an actuating finger 120 the actuating finger being arranged to protrude through the slot 130 in the actuator retaining wall and into contact with the cam wheel actuator 121. Each actuator finger 120 has an inclined camming surface 120a which in this embodiment has a sloping angle complimentary to that of the inclined surface 121a of the camming slot of the cam wheel actuator 121.

Located forwardly of the cam wheel actuator 121 is a grasping cam wheel 118 which is identical in form to actuating cam wheel 122. Grassing cam wheel 118 is held in place by virtue of its annular rim portion 118a being held between an in-turned end wall 117c of the actuator retaining capsule 117 and an end face of the actuator cam release member 119. In front of the grasping cam wheel 118 and slidably mounted on the actuating rod 111 is grasp releasing ring 116 which has a pair of generally conical surfaces 116a and 116b. The radially inner edge of the rearwardly facing surface 116b is radiussed, for reasons which will become apparent below.

Encircling the forwardly facing conical surface 116a of the grasp releasing ring 116 is grasp releasing actuator wheel 115 which comprises an array of spoke-like radial actuator elements 115a linked together at their radial outer ends by a thin flexible annulus 115b. The annulus 115b lies outside the actuator retaining capsule 117 and the actuator elements 115a extend into the interior of the capsule 117 through slots 117d. The actuator elements 115a protrude between adjacent pairs of actuator arms 131 and the flexible annulus 115b encircles the array of actuator arms 131, forming an annular bulge in the boot 114 which allows easy visual location of the grasp releasing mechanism.

In use, the handle of the instrument is held in a pen grip as with the instrument of FIGS. 1 and 2. In order to close the jaws of a surgical tool at the end of the shaft, the user depresses any one or more of the actuator arms 131 arranged around the circumference of the handle. Depressing the actuator arm 131 causes the inclined camming surface of the associated actuating finger 120 to be urged into a camming slot 121c of the cam wheel actuator 121 and into contact with the inclined surface of the camming slot 121c. As the inclined camming surface 120a of the actuating finger cams along the inclined surface 121a of the cam wheel actuator, it causes the cam wheel actuator 121 to be urged rearwardly along the spigot portion 119a of the actuator cam release member 119. This in turn has the effect of urging the actuating cam wheel 122 rearwardly against the biasing force of the first return spring 123 and, since the cams of actuating cam wheel 122 are in tight gripping contact with the actuating rod 111, also causes the actuating rod 111 to move rearwardly thereby causing the jaws of the tool to close. In the absence of the grasping cam wheel 118, the force of the second return spring 125 would cause the annular member 124 to push the actuator rod 111 back along the effector tube 112 thereby opening the jaws of the tool at the end of the shaft. However, because the cams of the grasping cam wheel 118 are in gripping contact with the actuating rod 111, the rod 111 is prevented from moving back along the effector tube 112 and thus the tool remains locked in the grasping position. In order to release the actuator shaft, the user depresses the grasp releasing actuator wheel 115 at any point or points on its circumference, thereby urging the spoke-like radial actuator elements 115a inwardly and into contact with the forward conical surface 116a of the grasp releasing ring 116. As the inclined surface of the actuator element 115a cams along the conical surface 116a, it forces the grasp releasing ring 116 in a rearwards direction against the grasping cam wheel 118. The flexibility of the thin web portion 118b of the grasping cam wheel 118 enables the grasp releasing ring 116 to force the radially innermost grasping portions (cams) of the cam wheel 118 slightly apart thereby releasing their grip on the actuating rod 111 which is then restored to its rest position by the force of the second return spring 125, and the jaws of the tool at the end of the shaft are caused to open.

The surgical instrument shown in FIG. 3 is designed such that the effector tube and actuating rod can be removed and disposed of at the end of each surgical operation, or alternatively sterilised and re-used. Removal of the effector tube 112 is achieved simply by unscrewing it from the junction member 113. The actuating rod 111 is then removed by pulling it out from the handle 101. Although the grassing cam wheel 118 and the actuating cam wheel 122 initially act to prevent retraction of the actuating rod from the handle, the gripping effect of the grasping cam wheel 118 is released by depressing the surface of the grasp releasing actuator wheel 115 in the manner described above whilst the gripping effect of the actuating cam wheel 122 is automatically released as the grasping portions 122c are pulled against the inclined surface of the actuator cam release member 119 which leads to the grasping portions 122c being forced a art sufficiently to release the actuating rod 111.

Once the actuating rod and effector tube have been removed, the handle and actuator mechanism in the handle may be sterilised for reuse. At the start of the next surgical procedure, a new actuating rod 111 and effector tube 112 arrangement may simply be fitted by pushing the actuating rod into the handle until it engages and is gripped by the grasping cam wheel 118 and actuating cam wheel 122 and then screwing the effector tube 112 into place as described above. By making the actuator rod and effector tube disposable, the potential problem of blood, other bodily fluids and tissue contaminating the instrument is avoided.

FIGS. 4 to 7b illustrate grasping forceps in accordance with a third embodiment of the invention. As with the embodiment shown in the previous Figures, the grasping forceps has a handle, a shaft and a surgical tool (not shown) mounted at its end. The handle is shaped so as to enable it to be held in a pen-like grip between thumb forefinger and index finger and, as with the previous embodiments, has a bulbous region at approximately its mid-point, and a pen-handle tail piece. From the exterior, the grasping forceps appear very similar to the instruments of FIGS. 1 to 3. However, the bulbous region conceals a modified actuation mechanism.

Figure 4:
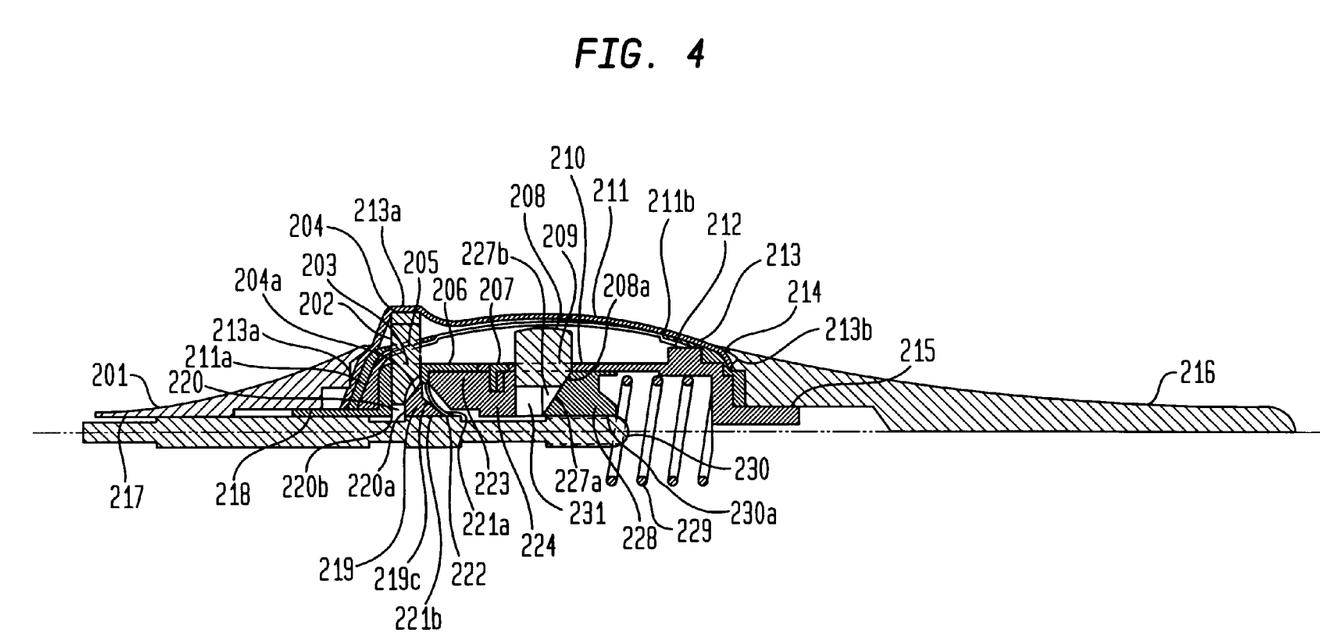
FIG. 4 is a partial sectional elevation of a surgical instrument according to a third embodiment of the invention.
Figure 5:
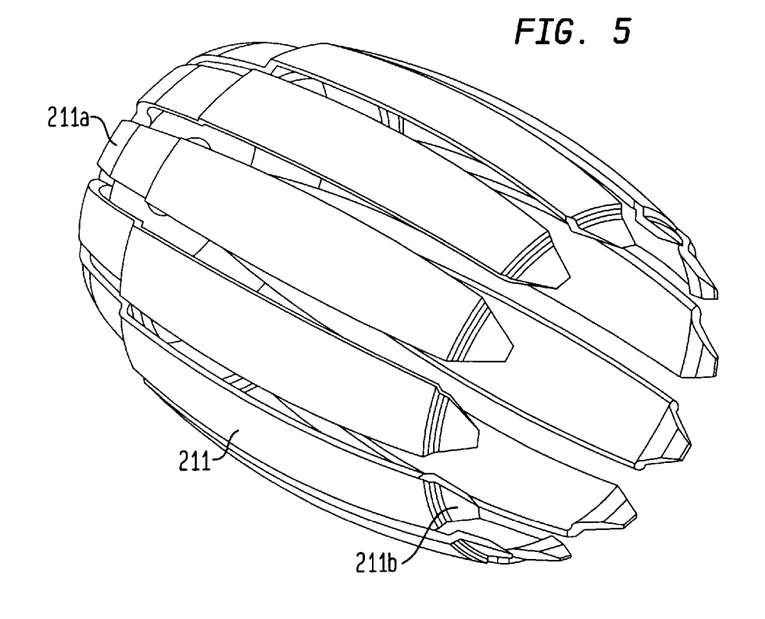
FIG. 5 is an isometric view of a component of the instrument shown in FIG. 4.

The actuation mechanism comprises a generally cylindrical housing (hereinafter referred to as the actuator retaining capsule) formed from a front capsule portion 206 and a rear capsule portion 210 each of generally closed ended cylindrical form. The two capsule portions 206 and 210 are connected together by means of a capsule junction block 224. The rear end of the capsule junction block 224 is received within the end of rear capsule portion 210 and is held in place by means of a pair of screws 207, only one of which is shown in the drawings. The leading portion of the capsule junction block 224 has an external thread 223 which engages an internal thread on the front capsule portion 206. Rear capsule portion 210 has extending rearwardly therefrom a threaded spigot 215 which engages an internal thread on the tapering pen-handle tail piece 216. The front capsule portion 206 also has a threaded spigot 218, onto which is screwed internally threaded junction member 201. The inner surface of the distal end of the junction member has a thread 217 into which the effector tube (not shown) can be screwed.

A cam wheel actuator 228 is slidably disposed within the rear end of the actuator retaining capsule. Cam wheel actuator 228 has a central bore which is threaded to engage and retain a correspondingly threaded end of the actuating rod 230. Cam wheel actuator 228 is biased forwardly by means of return spring 229.

As with the instruments illustrated in FIGS. 1 to 3, the cam wheel actuator has a plurality (in this case 12) of inclined surfaces 227a around its outer circumference, each inclined surface 227a being separated from an adjacent inclined surface by means of axially aligned dividing walls 227b. The inclined surfaces 227a and dividing walls 227b, together with the radial slots 231 of rear surface 224a of the capsule junction block 224 define pockets into which actuating wedges 208 are located. Actuating wedges 208, which are shown in enlarged form in FIGS. 7a and 7b, extend outwardly through slots 209 in the wail of rear capsule portion 210. The radially innermost ends of the actuating wedges 208 are tapered to allow them to be depressed closer to the central axis. An array of generally arcuate actuating arms 211 are arranged about the capsule such that their mid-sections bear against and hold in place the actuating wedges 208. The actuating arms 211 are linked at one end by means of a common hub 211a, the arrangement of the arms 211 with respect to the hub 211a being shown in FIG. 5. The hub 211a sits about the spigot 218 of the forward capsule portion and is surrounded by an annular collar 202. The ends 211b of the actuating arms remote from the common hub 211a taper and are retained within scalloped recesses 212 in an annular flange extending radially outwardly from the rear capsule portion. The ends 211b of the arms are held in place in the scalloped recesses by means of an annular collar 214 which encircles the end of the rear capsule portion 210.

The actuator retaining capsule, actuating wedges 208 and actuating arms 211 are surrounded and concealed by a flexible boot 213 formed of an appropriately flexible thin plastics material. The flexible boot 213 has in-turned end portions 213a and 213b which are clamped between the junction portion 201 and the front capsule portion 206, and the pen-handle tail piece 216 and rear capsule portion 210 respectively.

In use, actuation of the tool is achieved by depressing the flexible boot 213 and underlying actuating arms 211 and actuating wedges 208 to force the actuating wedges 208 radially inwardly in the slots 231. As the actuating wedges 208 move radially inwardly, so the inclined surfaces 208a cam along the inclined surfaces 227a of the cam wheel actuator 228 thereby urging the cam wheel actuator 228 against the force of return spring 229 in a rearwards direction. Since the actuating rod 230 is screwed into the cam wheel actuator 228, the actuating rod is also moved rearwardly thereby actuating the surgical tool at the end of the actuator shaft in a manner similar to that described in relation to FIGS. 1 to 3.

When pressure on the flexible boot 213, actuating arm 211 and actuating wedge 218 is released, the cam wheel actuator and actuating rod 230 remain locked in the retracted position, thanks to a grasping mechanism mounted in the capsule portion, as will now be described.

Figure 6:
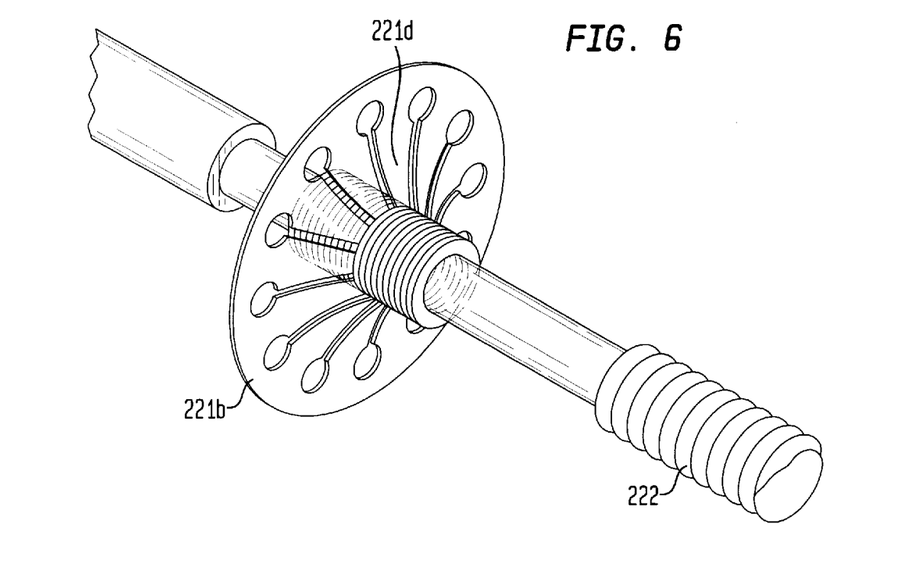
FIG. 6 is an isometric view of the grasping mechanism of the instrument shown in FIG. 4.
Figure 7A:
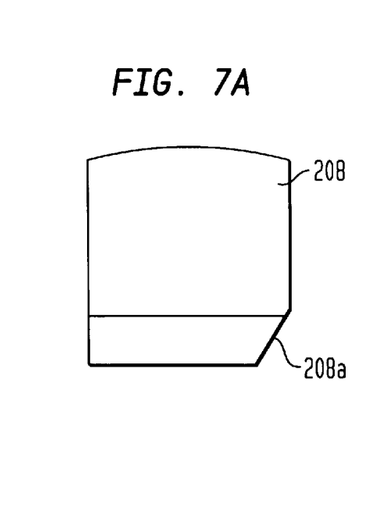
FIGS. 7a and 7b are enlarged elevations of actuating wedges and grasp releasing wedges respectively used in the instrument of FIG. 4.
Figure 7B:
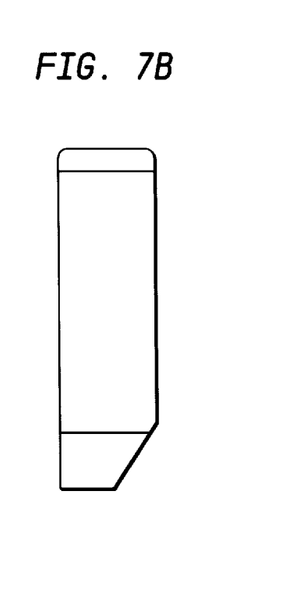

As can be seen from FIG. 4 and FIG. 6, the actuating rod 230 has a threaded end 230a which screws into the cam wheel actuator 228 and a second threaded region 222 which has a much finer thread (smaller pitch) than threaded end 220a. A pair of disc springs 221a and 221b surround the finely threaded region 222 on the actuating rod 230 and are clamped in place between opposing surfaces 206b and 224b of the front capsule portion 206 and capsule junction block 224 respectively.

The disc springs 221a and 221b, which are formed from a suitably resilient metal material, each have a plurality of (in this case twelve) of radially inwardly directed grasping fingers 221c, 221d. The rear disc spring 221b has an inner diameter slightly less than the outer diameter of the finely threaded region 222 on the actuating rod 230. The forward disc spring 221a has an inner diameter larger than the outer diameter of the finely threaded region 222. Disposed about the finely threaded region 222 and forwardly of the disc springs is a grasp releasing cam wheel 219 which has a plurality of inclined camming surfaces 220a separated by axially aligned dividing walls 220b which together define angled slots 220. The rear surface of the grasp releasing cam wheel 219 is provided with a second inclined camming surface 219a.

In this embodiment, the grasp releasing cam wheel 219 has an array of twelve angled slots 220 and these are staggered relative to the slots 231 defined by the capsule junction block 224 and cam wheel actuator 228. Each slot 220 has disposed therein a grasp releasing wedge 204, the radially outer end of which protrudes through slots 205 in the front capsule portion 206, between the actuating arms 211, and through slots 203 in the annular collar 202. The radially outer ends of the grasp releasing wedges 204 are accommodated within an annular bulge 213a in the flexible boot 213.

In use, as the actuator mechanism is actuated to move the actuating rod 230 in a rearwards direction towards the user, the fine thread 222 and the grasping fingers 221d of the rear disc spring 221b cooperate to form a ratchet mechanism which holds the actuating rod 230 in the retracted position against the forward biasing force of the return spring 229. In this way, a grasping forceps tool at the forward end of the instrument can be locked in a clamping or grasping position. The effect is to give a large number of grasping positions within a short travelling distance of the actuating rod 230 (number of positions=[travel÷pitch]×number of fingers, typically [1.5÷0.25]×12=72).

When it is desired to release the actuating rod 230, one or more of the grasp releasing wedges 204 are depressed such that the inclined camming surfaces 204a on the grasp releasing wedges 204 cam along the inclined surfaces 220a of the angled slots 220 to urge the grasp releasing cam wheel 219 in a rearwards direction. As the grasp releasing cam wheel 219 moves in a rearwards direction, it lifts the fingers 221d of the rear disc spring 221b away from the finely threaded portion 222 thus releasing their grasp on the actuating rod 230. The actuating rod 230 is then free to move in an axial direction and is urged forwardly again by the return spring 229. At the same time, the forward disc spring 221a acts as a return spring for the grasp releasing cam wheel 219 and urges it forwardly against the grasp releasing wedges 204 thereby displacing the grasp releasing wedges 204 outwardly to their rest position.

Figure 8:
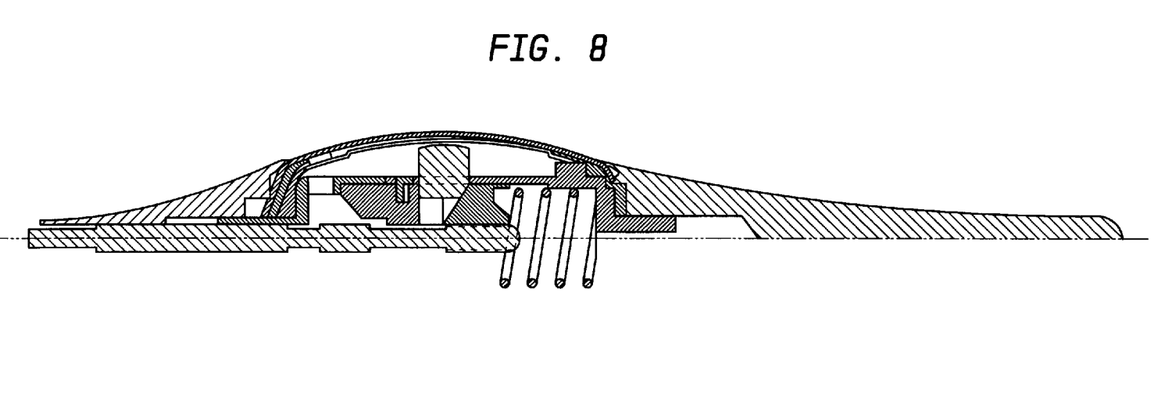
FIG. 8 is a partial sectional elevation of an instrument according to a fourth embodiment of the invention.

FIG. 8 illustrates a simple forceps arrangement which makes use of the same actuator retaining capsule and actuating arrangement as shown in FIG. 4 but omits the grasping/locking mechanism and the grasp releasing mechanism at the forward end of the capsule. Thus in this embodiment, depression of the actuating arms 211 and actuating wedges 208 displaces the cam wheel actuator 228 rearwardly against the force of the return spring 229, but once the pressure on the actuating arms 211 and actuating wedges 208 is released, the return spring 229 restores the cam wheel actuator and hence the actuating rod 230 to its original position. Thus, as with the surgical instrument of FIG. 1, the instrument of FIG. 8 provides only a simple "open and close" mechanism.

Figure 9:
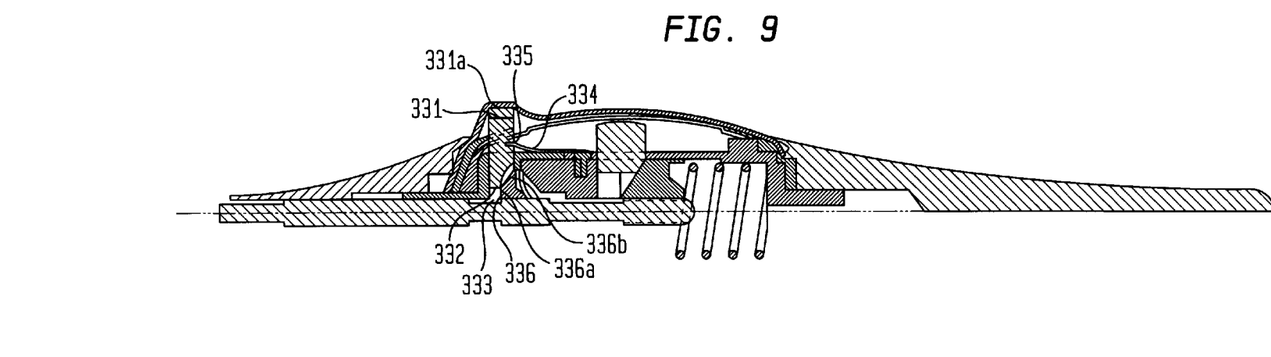
FIG. 9 is a partial sectional elevation of an instrument according to a fifth embodiment of the invention.

FIG. 9 illustrates a further modification to the grasping forceps shown in FIG. 4. In this embodiment, one of the grasp releasing wedges 204 is replaced by a grasp disabling wedge 331 the shape of which is illustrated more clearly in FIG. 10. The grasp disabling wedge is similar in shape to the grasp releasing wedge 204 in the embodiment of FIG. 4 except that it is slightly longer and the radially inner end of the wedge has a hooked shape or toe 332 defined by inclined surfaces 332a and 332b. The corresponding guide slot 333 has a cut away region or overhang 336 defined by inclined surface 336a and ridge 336b. The grasp disabling wedge 331 is biased radially outwardly by means of a biasing leaf spring 334 which is mounted at one end in a slot 335 on the grasp releasing wedge 331 and at the other end is secured to the outer surface of the capsule by means of a retaining screw (not shown). The grasp disabling wedge 331 stands proud of the grasp releasing wedges 211 and the radially outer end 331a of the grasp disabling wedge is located in a small radial extension of the annular bulge on the flexible boot 213.

Figure 10:
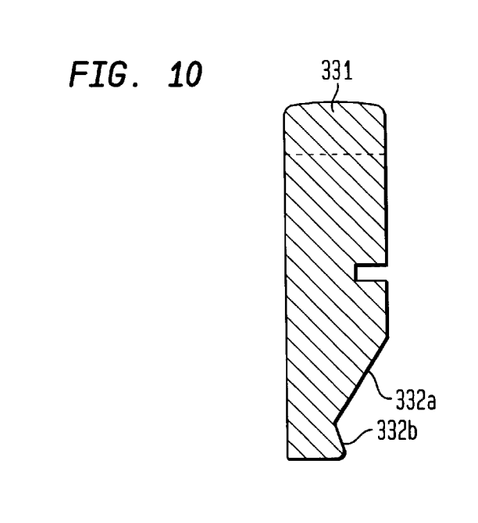
FIG. 10 is an enlarged cross-section of a component of the instrument shown in FIG. 9.

In use, in order to disable the grasping mechanism, the grasp disabling wedge 331 is depressed, along with some of the grasp releasing wedges 204, such that hook or toe 332 snaps over the ridge 336b and, in so doing, the grasp releasing cone is urged in a rearwards direction to lift the grasping fingers 221d of the disc spring 221b away from the fine threaded region 222. On releasing, the grasp disabling wedge 331 prevents the fingers 221d from re-engaging thus disabling the grasping mechanism. When the instrument is subsequently actuated by depressing the actuating arms 211 and actuating wedges 208, since the ratchet mechanism defined by the fine thread region 222 and the disc spring 221b has been disabled, the return spring 229 restores the actuating rod 230 to its original position when the pressure on actuator fingers 211 and actuator wedges 208 is released.

In order to re-enable the grasping mechanism, one or more of the eleven grasp releasing wedges 204 are depressed thus urging the grasp releasing cone 219 in a rearwards direction, thereby releasing the grasp disabling wedge 331 which is restored to its rest position by the return spring 334.

Figure 11:
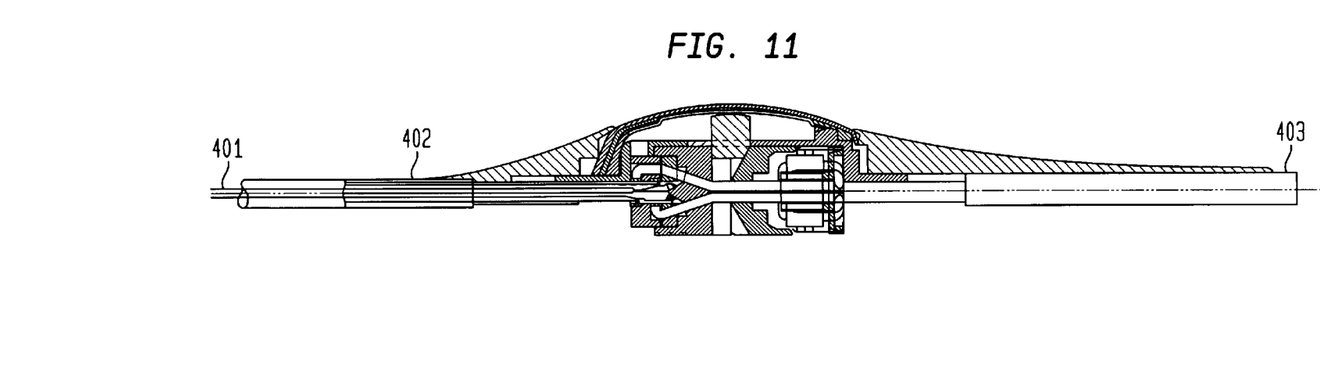
FIG. 11 is a partial sectional elevation of a surgical instrument according to a sixth embodiment of the invention.
Figure 12:
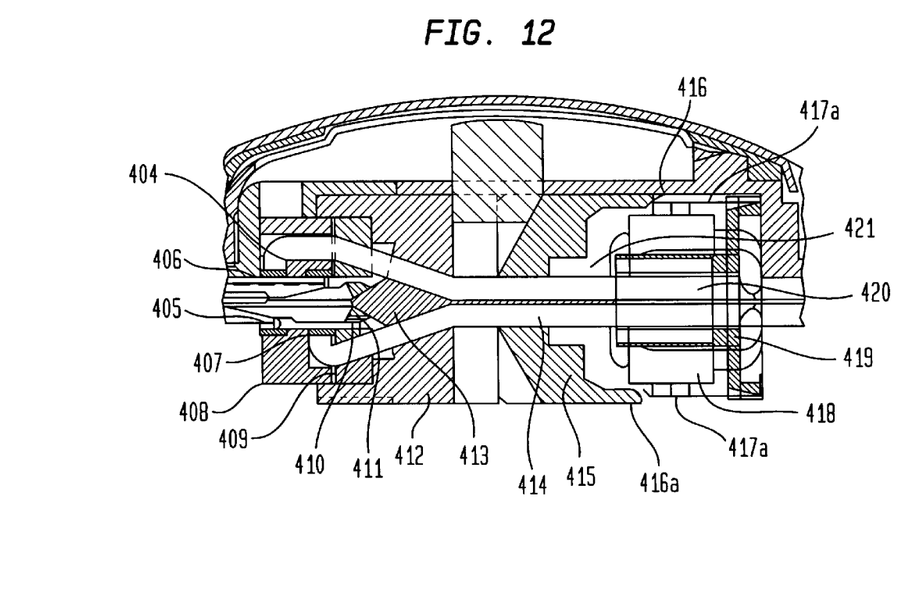
FIG. 12 is an enlarged view of cart of the surgical instrument shown in FIG. 11.

FIGS. 11 and 12 illustrate a further embodiment of the invention in the form of a diathermy instrument. In this embodiment, the actuating mechanism is similar to that shown in the preceding embodiments, except that the mechanical components of the actuator retaining capsule have been largely replaced by electrical components.

As shown in FIGS. 11 and 12, the actuating mechanism comprises an actuator retaining capsule, actuating wedges and an array of actuating fingers surrounded by a flexible boot of the same type as shown in FIG. 4, the simple forceps arrangement. The two halves of the actuator capsule are held together by means of junction block 412 which is threaded to engage corresponding threads on the front capsule portion, and is secured to rear capsule portion by means of screws (not shown). In this embodiment however, the junction block is modified in shape to accommodate electrical contact block 408 and wiring location ring 409.

The rear portion of the actuator retaining capsule contains a cam wheel actuator 415 having an axially short contacting surface 416a and an axially longer contacting surface 416b. Mounted behind the cam wheel actuator 415 within recess 421 are a pair of micro switches 418 and micro switch contact springs 417a and 417b. Contact springs 417a and 417b are connected by means of an annular ring which is held in place by clamping between switch block 419 and the inner end wall of the rear capsule portion. A power supply cable 403 enters the Den-handle tail piece of the tool and extends into the capsule where it is connected to micro switches 418 and capacitors 420. Wires 414 extend between micro switches 418 and actuator contact rings 406 and 407 in the forward part of the actuator capsule. Electrical contacts 404 and 405 protruding from the effector end 410 engage the actuator contact rings 406 and 407 respectively and electrical wires 401 extend along the interior of the effector tube to a diathermy hook (not shown) at the end thereof.

The effector tube end 410, which has an axial split 411, abuts against a conical portion 413 of the junction block 412. As the effector tube is screwed into the conical junction member by means of thread 402, the two halves of the split end of the effector tube 410 are forced apart by the conical portion 413 thereby ensuring positive contact between the electrical contacts 404 and 405 and the actuator contact rings 407 and 406 respectively.

In use, the diathermy instrument is actuated in a similar manner to the instruments shown in FIGS. 1 to 10; i.e. the actuator arms and actuator wedges arrangement surrounding the retaining actuator capsule are depressed so as to urge the cam wheel actuator 415 in a rearwards direction. An inclined surface 416b on the cam wheel actuator 415 cams along the in-turned end of micro switch contact spring 417b to depress the micro switch thereby switching on a source of current to the effector contact 404. The current provided by switch 417a is sufficient to provide enough heat at the diathermy hook for coagulation, but is insufficient to generate a temperature which can efficiently cut through tissue. When it is desired to use the diathermy hook to cut through tissue, the actuator arm 411 and actuator wedge 408 are further depressed so as to displace the cam wheel actuator 415 rearwardly such that the shorter actuator contacting surface 416a engages the in-turned end of micro switch contact spring 417a to actuate micro switch 418a. This permits a current suitable for tissue cutting to flow through the wires along the effector rod to the diathermy hook. On releasing, the actuator cam wheel 415 is returned to its rest position by a return spring (not shown) contained in cavity 421, and acting on the rear of the actuator cam wheel 415 and the end of a cavity in the switch block 419.

It will readily be apparent that numerous modifications and alterations may be made to the surgical instruments shown in the drawings and specifically described above, without departing from the principles underlying this invention. All such modifications and alterations are intended to be embraced by this application.

What is claimed is:

1. A surgical instrument comprising a handle shaped to enable it to be freely rotated by the user's fingers about its longitudinal axis in the hand of the user, and held by the user at any angle of rotation about its longitudinal axis; the handle having an elongate shaft extending therefrom and a surgical tool mounted on the shaft at a location remote from the handle; the handle being provided with an actuator operably linked to the surgical tool, the actuator being mechanically linked to an actuating rod disposed slidably within the elongate shaft, which rod is in turn linked to the surgical tool on the end of the shaft, the actuating rod having a camming edge or surface associated therewith; the actuator having an actuator surface or surfaces extending around substantially the entire circumference of the handle and comprising a plurality of radially displaceable actuator elements disposed around the circumference of the handle, each actuator element being provided with a wedging member; the actuator being operable by applying pressure at substantially any circumferential location on the actuator surface or surfaces to urge a said actuator element radially inwardly such that the wedging member of the said actuator element cams against the camming edge or surface associated with the actuating rod to displace the camming edge or surface in a longitudinal direction thereby converting radially inward movement of the actuator element into longitudinal movement of the actuating rod within the elongate shaft so as to actuate the surgical tool.

2. A surgical instrument according to claim 1, wherein each wedging member has an inclined surface whereby radially inward movement of the actuator element urges the inclined surface of the wedging member into contact with the said camming edge or surface associated with the actuator shaft, thereby to displace the camming edge or surface in a longitudinal direction.

3. A surgical instrument according to claim 1, wherein the actuator surface is a continuous surface extending around the circumference of the handle.

4. A surgical instrument according to claim 1, having at least three actuator elements.

5. A surgical instrument according to claim 4, wherein there are at least six actuator elements.

6. A surgical instrument according to claim 1, wherein the handle is of elongate form and is sufficiently small in cross-section to enable it to be held in a pen-like grip.

7. A surgical instrument according to claim 6, wherein the handle has a bulbous shape, being tapered towards the end remote from the surgical tool, increasing in diameter towards the central portion thereof and tapering again towards the actuator shaft.

8. A surgical instrument according to claim 7, wherein the actuator means is located within the bulbous or enlarged diameter central portion of the handle.

9. A surgical instrument according to claim 1, wherein the handle is provided with means for effecting locking of the surgical tool in a given configuration.

10. A surgical instrument according to claim 9, wherein the surgical tool is in the form of a miniature pair of grasping forceps or a clamping tool and the locking means is effective to lock the forceps or clamping tool in a clamping or gripping configuration.

11. A surgical instrument according to claim 9, wherein the handle is provided with first actuator means for effecting movement of a surgical tool at the end of the actuator shaft from a rest position to an actuated position; locking means for locking the surgical tool in the actuated position; and second actuator means operable to release the locking means to enable the surgical tool to return to the rest position.

12. A surgical instrument according to claim 11, wherein the actuator is mechanically linked to an actuating rod disposed slidably within the elongate shaft, which rod is in turn linked to the surgical tool on the end of the shaft, the locking means taking the form of a grasping member having a plurality of grasping portions which grasp the actuating rod to lock it in an actuating position, the second actuator means being operable to force the said grasping portions apart to release the grip on the actuating rod.

13. A surgical instrument according to claim 12, wherein the actuating rod is provided with a spiral track or an array of annular ridges which cooperate with the grasping portions to form a ratchet mechanism.

14. A surgical instrument according to claim 13, wherein the spiral track is a fine thread.

15. A surgical instrument according to claim 11, wherein the second actuator means is arranged to be actuable from substantially any position around the circumference of the handle.

16. A surgical instrument according to claim 12, wherein the plurality of grasping portions take the form of an annular array of radially inwardly directed grasping fingers formed from a resilient material.

17. A surgical instrument according to claim 16, wherein the annular array of radially inwardly grasping fingers are constituted by a metal disk spring.

18. A surgical instrument according to claim 16, wherein the clearance between the radially inner most edges of opposing grasping fingers is less than the diameter of the actuating rod; such that as the actuating rod is urged through the grasping means in one direction, the grasping fingers engage the spiral track at the surface of the actuating rod to prevent movement of the actuating rod in the reverse direction.

19. A surgical instrument according to claim 16, having grasp releasing means in the form of a grasp releasing member having a conical or frustoconical surface which can be urged in an axial direction against the grasping fingers to lift them away from the spiral track to release the actuating rod.

20. A surgical instrument comprising a handle shaped to enable it to be freely rotated by the user's fingers about its longitudinal axis in the hand of the user, and held by the user at any angle of rotation about its longitudinal axis; the handle having an elongate shaft extending therefrom and a surgical tool mounted on the shaft at a location remote from the handle; the handle being provided with a first actuator means operably linked to the surgical tool for effecting movement of the surgical tool from a rest position to an actuated position, the first actuator means being mechanically linked to an actuating rod disposed slidably within the elongate shaft, which rod is in turn linked to the surgical tool on the end of the shaft; the actuator means having an actuator surface or surfaces extending around substantially the entire circumference of the handle and comprising a plurality of radially displaceable actuator elements disposed around the circumference of the handle, whereby the first actuator means is operable by applying pressure at substantially any circumferential location on the actuator surface or surfaces to actuate the surgical tool, means being provided for converting radial inward movement of an actuator element into longitudinal movement of the actuating rod within the elongate shaft; the means for converting radial inward movement of the actuator element into longitudinal movement of the actuating rod comprising an edge or surface of the actuator element which functions as a cam follower or camming surface, for engaging and camming against a complimentary camming surface or cam follower associated with the actuating rod; the handle being further provided with locking means for locking the surgical tool in the actuated position, and second actuator means operable to release the locking means to enable the surgical tool to return to the rest position, the second actuator means being actuable from substantially any position around the handle.

21. A surgical instrument according to claim 20, wherein the surgical tool is in the form of a miniature pair of grasping forceps or a clamping tool and the locking means is effective to lock the forceps or clamping tool in a clamping or gripping configuration.

22. A surgical instrument according to claim 20, wherein the actuator means is mechanically linked to an actuating rod disposed slidably within the elongate shaft, which rod is in turn linked to the surgical tool on the end of the shaft, the locking means taking the form of a grasping member having a plurality of grasping portions which grasp the actuating rod to lock it in an actuating position, the second actuator means being operable to force the said grasping portions apart to release the grip on the actuating rod.

23. A surgical instrument according to claim 22, wherein the actuating rod is provided with a spiral track or an array of annular ridges which cooperate with the grasping portions to form a ratchet mechanism.

24. A surgical instrument according to claim 23, wherein the spiral track is a fine thread.

25. A surgical instrument according to claim 22, wherein the plurality of grasping portions take the form of an annular array of radially inwardly directed grasping fingers formed from a resilient material.

26. A surgical instrument according to claim 25, wherein the annular array of radially inwardly grasping fingers are constituted by a metal disk spring.

27. A surgical instrument according to claim 25, wherein the clearance between the radially inner most edges of opposing grasping fingers is less than the diameter of the actuating rod; such that as the actuating rod is urged through the grasping means in one direction, the grasping fingers engage the spiral track at the surface of the actuating rod to prevent movement of the actuating rod in the reverse direction.

28. A surgical instrument according to claim 25, having grasp releasing means in the form of a grasp releasing member having a conical or frustoconical surface which can be urged in an axial direction against the grasping fingers to lift them away from the spiral track to release the actuating rod.

\* \* \* \* \*